United States Patent [19]

Weber et al.

[11] 4,235,741
[45] Nov. 25, 1980

[54] V-TRIAZOLES

[75] Inventors: Kurt Weber, Basel; Rudolf Kirchmayr, Aesch, both of Switzerland

[73] Assignee: Ciba-Geigy Corporation, Ardsley, N.Y.

[21] Appl. No.: 48,965

[22] Filed: Jun. 15, 1979

Related U.S. Application Data

[63] Continuation of Ser. No. 799,058, May 20, 1977, abandoned.

[30] Foreign Application Priority Data

Jun. 2, 1976 [CH] Switzerland ............ 6933/76
Jan. 28, 1977 [CH] Switzerland ............ 1071/77

[51] Int. Cl.$^3$ ............................................ C07D 249/06
[52] U.S. Cl. ......................... 252/301.22; 252/301.25; 542/432; 542/435; 542/452; 542/468; 542/462
[58] Field of Search ............... 542/462, 466, 452, 435, 542/432; 252/301.22, 301.25

[56] References Cited

U.S. PATENT DOCUMENTS

| | | | |
|---|---|---|---|
| 3,444,180 | 5/1969 | Maeder et al. | 542/459 |
| 3,485,831 | 12/1969 | Dorlars et al. | 542/462 |
| 3,579,511 | 5/1971 | Weber et al. | 542/462 |
| 3,732,221 | 5/1973 | Siegrist et al. | 542/459 |
| 3,761,470 | 9/1973 | Strobel et al. | 542/462 |
| 3,862,179 | 1/1975 | Kabas et al. | 542/458 |
| 3,899,487 | 8/1975 | Fleck et al. | 260/308 A |
| 4,001,221 | 1/1977 | Günther et al. | 260/308 A |
| 4,014,871 | 3/1977 | Kormany et al. | 260/308 A |
| 4,032,558 | 6/1977 | Fleck et al. | 542/460 |
| 4,039,531 | 8/1977 | Günther et al. | 542/458 |

FOREIGN PATENT DOCUMENTS 2238734 2/1973 Fed. Rep. of Germany .
2525637 2/1976 Fed. Rep. of Germany .

OTHER PUBLICATIONS

Drefahl et al., Chem. Ber. 93(1960), pp. 492-497.

*Primary Examiner*—Arthur P. Demers
*Attorney, Agent, or Firm*—Prabodh I. Almaula

[57] ABSTRACT

Novel 2,4-Bis-(stilben-4'-yl)-v-triazoles of the formula

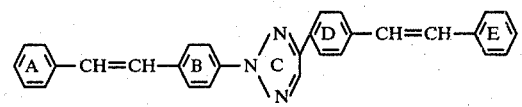

wherein the rings A, B, C, D and E can contain certain nonchromophoric substituents, methods for their preparation as well as their use as optical brighteners are disclosed.

15 Claims, No Drawings

V-TRIAZOLES

This is a continuation of application Ser. No. 799,058 filed on May 20, 1977, now abandoned.

The present invention provides novel 2,4-bis-(stilben-4'-yl)-v-triazoles and a method of optically brightening organic material which comprises the use thereof.

The novel 2,4-bis-(stilben-4'-yl)-v-triazoles have the formula

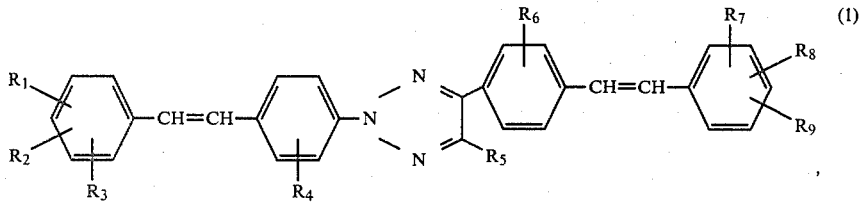

wherein
each of
  $R_1$ and $R_7$ independently represents a hydrogen atom, a sulphonic acid group or the salts, esters or amides thereof, a carboxylic acid group or the salts, esters or amides thereof, a cyano group, a halogen atom, an unsubstituted or substituted alkylsulphonyl, arylsulphonyl, alkyl, alkoxy, aralkyl, aryl, aryloxy, aralkoxy or cycloalkyl radical, an unsubstituted or substituted 5-membered heterocyclic ring containing 2 to 3 nitrogen atoms or one oxygen atom and 1 or 2 nitrogen atoms, or together with $R_2$ and $R_8$ they represent a methylenedioxy, ethylenedioxy, methylenoxymethylenoxy, trimethylene, tetramethylene, propenylene, butenylene or butadienylene radical,
each of
  $R_2$ and $R_8$ independently represents a hydrogen atom, a sulphonic acid group or the salts, esters or amides thereof, a carboxylic acid group or the salts, esters or amides thereof, a cyano group, a halogen atom, an unsubstituted or substituted alkyl or alkoxy radical, or together with $R_1$ and $R_7$ represent a methylenedioxy, ethylenedioxy, methylenoxymethylenoxy, trimethylene, tetramethylene, propenylene, butenylene or butadienylene radical,
each of
  $R_3$ and $R_9$ independently represents a hydrogen atom, a halogen atom or an unsubstituted or substituted alkyl radical,
each of
  $R_4$ and $R_6$ independently represents a hydrogen atom, a halogen atom, a cyano group, a sulphonic acid group or the salts, esters or amides thereof, or a carboxylic acid group or the salts, esters or amides thereof, and
  $R_5$ represents a hydrogen atom, a halogen atom, a cyano group, a sulphonic acid group or the salts, esters or amides thereof, a carboxylic acid group or the salts, esters or amides thereof, an unsubstituted or substituted alkyl, aryl, aralkyl or styryl radical or the —$CH_2OZ$ group, in which Z represents a hydrogen atom or an unsubstituted or substituted aroyl or alkanoyl radical.

Alkylsulphonyl radicals can be substituted by phenyl, hydroxy, alkanoyloxy of 2 to 15 carbon atoms or by halogen. Arylsulphonyl radicals can be substituted preferably by halogen or alkyl of 1 to 8 carbon atoms, and alkyl radicals preferably by hydroxy, alkoxy of 1 to 4 carbon atoms, cyano, halogen, carboxy, sulphonic acid groups, carbalkoxy having 1 to 4 carbon atoms in the alkoxy moiety, phenyl or phenoxy. Alkoxy radicals can be substituted by hydroxy, alkoxy of 1 to 4 carbon atoms, cyano, halogen, carboxy, carbalkoxy having 1 to 4 carbon atoms in the alkoxy moiety, phenyl or phenoxy. Phenyl, phenylalkyl or phenoxy radicals can be substituted by halogen, cyano, carboxy, carbalkoxy having 1 to 4 carbon atoms in the alkoxy moiety, sulpho, or alkyl or alkoxy each of 1 to 4 carbon atoms. Possible cycloalkyl radicals are preferably cyclohexyl and cyclopentyl radicals which can be substituted by alkyl of 1 to 4 carbon atoms. Possible 5-membered heterocyclic rings are v-triazole, oxazole or 1,3,4-oxdiazole radicals which can contain as substituents alkyl radicals of 1 to 4 carbon atoms, halogen, phenyl, carboxy, carbalkoxy having 1 to 4 carbon atoms in the alkoxy moiety, cyano, benzyl, alkoxy of 1 to 4 carbon atoms, phenoxy or sulpho, whilst two adjacent substituents of the triazole and oxazole radicals together are able to form a substituted or unsubstituted fused benzene nucleus.

Styryl radicals can contain the substituents referred to above in connection with phenyl radicals.

The term "halogen" is to be understood as meaning fluorine, chlorine and bromine, in particular chlorine and bromine, preferably chlorine.

Possible salts of the sulphonic and carboxylic acid groups are chiefly alkali metal, alkaline earth metal, ammonium or amine salts, in particular alkali metal salts.

Possible aroyl radicals are in particular mono- and binuclear radicals, preferably the benzoyl radical, and possible alkanoyl radicals are those containing a total of 2 to 19, preferably 2 to 5, carbon atoms.

2,4-Bis-(stilben-4'-yl)-v-triazoles falling within the scope of the formula (1) to be singled out for special mention are those of the formula

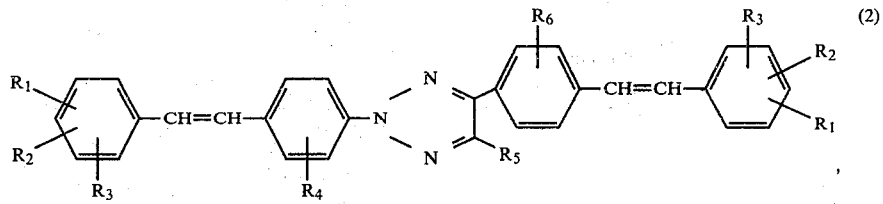

wherein $R_1$ to $R_5$ are as defined in formula (1).

Preferred 2,4-bis-(stilben-4'-yl)-v-triazoles are those of the formula

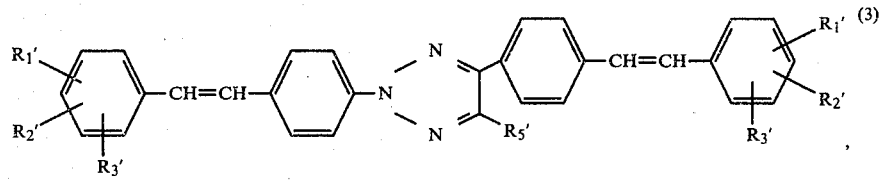

wherein
- $R_1'$ represents a hydrogen atom, a sulphonic acid group or the salts, esters or amides thereof, a carboxylic acid group or the salts, esters or amides thereof, a chlorine atom, a cyano group, an alkylsulphonyl group of 1 to 4 carbon atoms, a phenylsulphonyl group, an alkyl or alkoxy radical of 1 to 4 carbon atoms, a cyclohexyl, benzyl, benzoxazol-2-yl or phenyl radical,
- $R_2'$ represents a hydrogen atom, a sulphonic acid group or the salts thereof, a carboxylic acid group or the salts, esters or amides thereof, an alkyl radical of 1 to 4 carbon atoms or a chlorine atom,
- $R_3'$ represents a hydrogen or chlorine atom or an alkyl radical of 1 to 4 carbon atoms,
- $R_5'$ represents a hydrogen or chlorine atom, a cyano group, a carboxylic acid group or the salts, esters or amides thereof, an alkyl radical of 1 to 6 carbon atoms, a phenyl or benzyl radical which is unsubstituted or substituted by a chlorine atom or an alkyl radical of 1 to 4 carbon atoms, as well as, within the scope of the 2,4-bis-(stilben-4'-yl)-v-triazoles of the formula (2) and (3), those compounds wherein at least one of the symbols $R_1$ to $R_5$ or $R_1'$ and $R_2'$ represents a sulpho group or the salts thereof.

Particularly interesting 2,4-bis-(stilben-4'-yl)-triazoles falling within the scope of the formula (1) are those of the formula

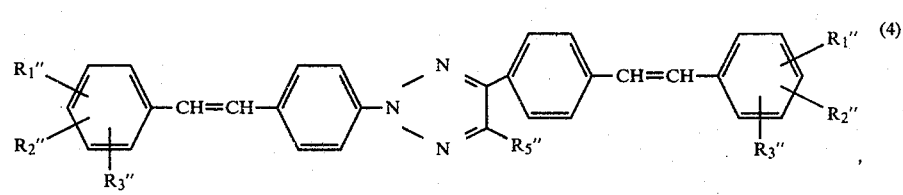

wherein
- $R_1''$ represents a hydrogen atom, a sulphonic acid group or the salts thereof, a carbalkoxy group having altogether 2 to 5 carbon atoms, a chlorine atom, a cyano group, an alkylsulphonyl radical of 1 to 4 carbon atoms, an alkyl or alkoxy radical each having 1 to 4 carbon atoms, a benzoxazol-2-yl or phenyl radical,
- $R_2''$ represents a hydrogen atom, a sulphonic acid group or the salts thereof or a chlorine atom,
- $R_3''$ represents a hydrogen or chlorine atom, and
- $R_5''$ represents a hydrogen or chlorine atom, an alkyl radical of 1 to 4 carbon atoms or a phenyl radical, those of the formula

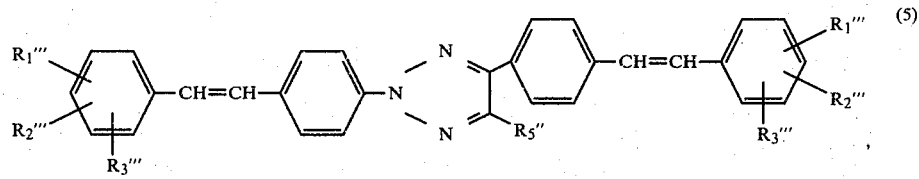

wherein
- $R_1'''$ represents a hydrogen atom, a sulphonic acid group or the salts thereof, a carbalkoxy group having altogether 2 to 5 carbon atoms, a chlorine atom, a cyano group, an alkylsulphonyl radical having 1 to 4 carbon atoms, an alkyl or alkoxy radical each having 1 to 4 carbon atoms, or a phenyl radical,
- $R_2'''$ represents a sulphonic acid group or the salts thereof,
- $R_3'''$ represents a hydrogen or chlorine atom, and
- $R_5'''$ represents a hydrogen or chlorine atom, an alkyl radical of 1 to 4 carbon atoms, or a phenyl radical, and those of the formula

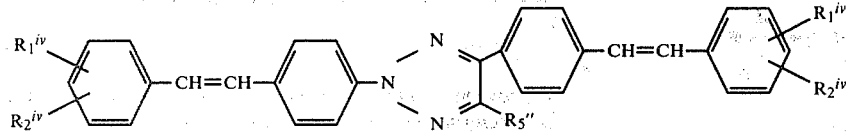

wherein
$R_1^{iv}$ represents a hydrogen atom, a carbalkoxy group having altogether 2 to 5 carbon atoms, a chlorine atom, a cyano group, an alkylsulphonyl radical having 1 to 4 carbon atoms, an alkyl or alkoxy radical each having 1 to 4 carbon atoms, a benzoxazol-2-yl or phenyl radical, $R_2^{iv}$ represents a hydrogen or chlorine atom, and $R_5''$ represents a hydrogen or chlorine atom, an alkyl radical of 1 to 4 carbon atoms or a phenyl radical.

Particularly interesting 2,4-bis-(stilben-4'-yl)-v-triazoles are those of the formula

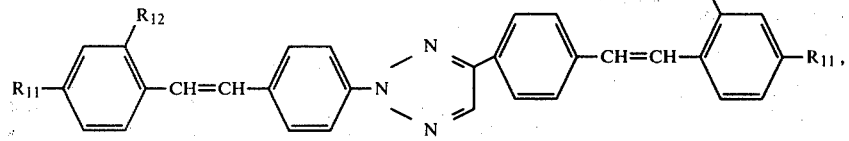

wherein
$R_{11}$ represents a hydrogen atom, a sulphonic acid group or the salts thereof, a cyano group, a phenyl radical, a chlorine atom, a carbalkoxy group having 2 to 5 carbon atoms or an alkylsulphonyl radical having 1 to 4 carbon atoms, and $R_{12}$ represents a hydrogen or chlorine atom or a sulphonic acid group or the salts thereof, whilst at least one of these two symbols represents a sulphonic acid group or the salts thereof, and those of the formula

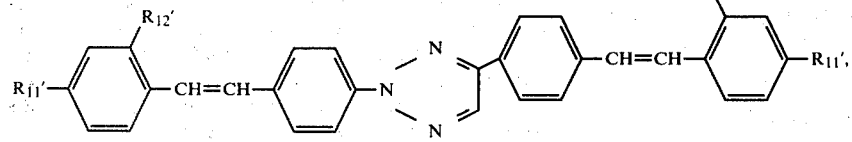

wherein
$R_{11}'$ represents a hydrogen atom, a cyano group, a phenyl radical, a chlorine atom, a carbalkoxy radical having 2 to 5 carbon atoms, a benzoxazol-2-yl radical or an alkylsulphonyl radical having 1 to 4 carbon atoms, and represents a hydrogen or chlorine atom.

$R_{12}'$ represents a hydrogen or chlorine atom.

Particularly preferred 2,4-bis-(stilben-4'-yl)-v-triazoles are those of the formula

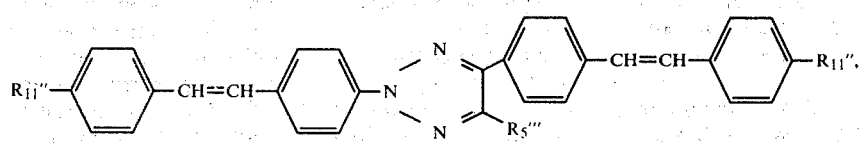

wherein $R_{11}''$ represents a cyano group, a carbalkoxy radical of 2 to 5 carbon atoms or an alkylsulphonyl radical of 1 to 4 carbon atoms, and $R_5'''$ represents a hydrogen or chlorine atom.

The 2,4-bis-(stilben-4'-yl)-v-triazoles of the formula (1) can be obtained by methods which are known per se. Thus those of the formula (2) can be obtained for example by reaction of 1 molar equivalent of a compound of the formula (10)

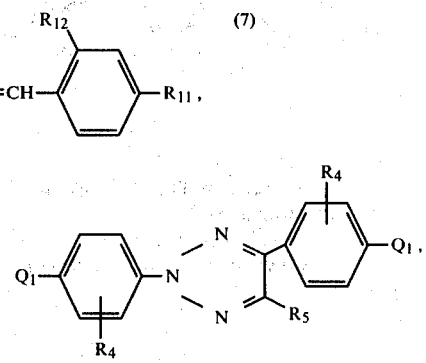

wherein $R_4$ and $R_5$ are as defined in formula (1), with two molar equivalents of a compound of the formula (11)

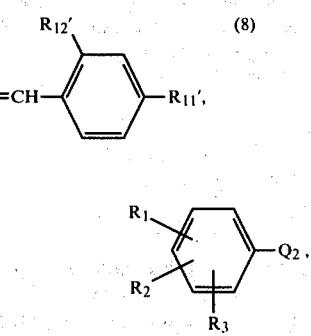

in which $R_1$, $R_2$ and $R_3$ are as defined in formula (1), and one of the symbols $Q_1$ and $Q_2$ in the above formulae represents a —CHO group and the other represents one of the groups of the formulae

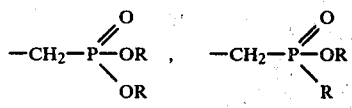

wherein R represents an unsubstituted or substituted alkyl, aryl, cycloalkyl or aralkyl radical, in the presence of a strong base and of a solvent.

It is also possible to obtain a number of 2,4-bis-(stilben-4'-yl)-v-triazoles of the formula (1), for example those of the formula

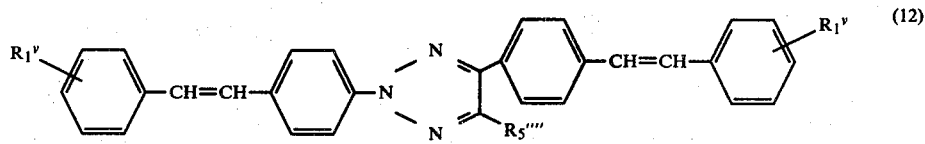

wherein
$R_1^v$ represents a hydrogen or chlorine atom, a methoxy or phenyl radical, and
$R_5''''$ represents a methyl or phenyl radical, by reacting one molar equivalent of a dimethyl compound of the formula

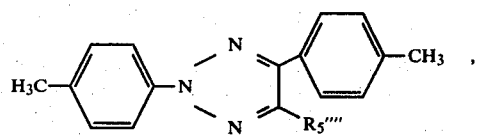

wheren $R_5''''$ is as defined in formula (12), in the presence of a basic alkali compound in a polar neutral to basic organic solvent, with 2 molar equivalents of a Schiff's base of the formula

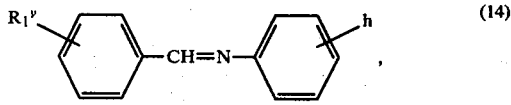

wherein $R_1^v$ is as defined in formula (12) and h represents a hydrogen or chlorine atom.

Suitable polar neutral to alkaline organic solvents are those which do not contain atoms, in particular hydrogen atoms, which an be replaced by alkali metals. In practice, suitable solvents of kind are chiefly dialkylamides of formic acid and phosphoric acid as well as tetralkylureas, wherein "alkyl" represents a lower $C_1$-$C_4$-alkyl, in particular methyl, group. Important examples of such solvents are: diethyl formamide, hexamethylphosphoric triamide, tetramethyl urea, and, in particular, dimethyl formamide. Solvent mixtures are also suitable.

As has been mentioned already, a strongly basic alkali compound is also necessary for carrying out the reaction. Suitable for this purpose, depending on the nature of the solvent and the reactivity of the anil, are specific sodium alcoholates, such as sodium tert.-butylate, and in particular potassium compounds of the composition $$KOC_{m-1}H_{2m-1} \quad (15),$$

wherein m is an integer from 1 to 6, preferably 2 to 6, for example potassium hydroxide, or especially potassium tert. butylate. When using such alkali alcoholates the process must be carried out in virtually anhydrous medium, whereas a small water content of up to app. 15% (e.g. water of crystallisation) is permissible when using potassium hydroxide. It is advantageous on occasion to use potassium hydroxide or sodium tert.-butylate, in combination with hexamethylphosphoric triamide at elevated temperature, e.g. at 110°–130° C. It will be readily understood that mixtures of such bases can also be used for carrying out the process.

The compounds containing methyl groups are reacted with the anils in equivalent amounts, i.e. in the molar ratio of 1:2, so that there is no substantial excess of either component. An excess of anil of up to approx. 50% is however usually advantageous. It is advantageous to use at least the equivalent amount of alkali compound, i.e. at least 1 mole of a compound with for example, one KO group to 1 mole of aldehyde anil. When using potassium hydroxide, it is preferable to do so in 4 to 8 times the equivalent amount. Particularly good yields are obtained on using potassium tert. butylate in one to six times, preferably two to four times, the equivalent amount.

The reaction can usually be carried out at temperatures in the range between about 10° and 150° C. When using particularly reactive anils, the reaction takes place at room temperature, in which case it is not necessary to apply heat externally. This is advantageous if the reactants contain ring compounds or substituents which can be easily opened or split off by alkali or which can be chemically changed in some other way. This applies, for example, to anils which contain chlorine substituents which can be easily split off. However, it is most advantageous to carry out the process at elevated temperature. For example, the reaction mixture is heated slowly to 30° to 80° C. and then kept at this temperature for a time, e.g. from ½ hour to 2 hours.

The manufacture of the anil and the reaction thereof with the tolyl compound can also be carried out consecutively in the one reaction vessel. For example, the aldehyde is heated with excess aniline in dimethyl formamide and the reaction mixture is complete evaporated to dryness in vacuo. The tolyl component and dimethyl formamide are added and the usual procedure is carried out.

The final products can be worked up from the reaction mixture by conventional methods which are known per se. The isolation is effected for example by precipitation with water, whilst water-soluble products are salted out, for example with NaCl, KCl or by neutralisation, if appropriate by acidification with a strong mineral acid, for example hydrochloric acid. In these last mentioned cases, the free sulphonic acids can be precipitated and can, if appropriate, be converted into the corresponding alkali metal, alkaline earth metal, ammonium or amine salts by reaction with alkali salts or alkaline earth salts or with ammonium hydroxide or amines. The amine salts of the sulphonic acids are also obtained for example by converting an alkali salt of the sulphonic acid into the sulphonyl chloride with phosphoroxy chloride, thionyl chloride, phosphorus pentachloride etc., and subsequent saponification in the presence of the desired amine.

The starting materials of the formulae (10), (11), (13) and (14) are known or can be prepared by methods analogous to known ones.

Compounds of the formula (10) are obtained for example by reacting an isonitrosoacetophenone of the formula

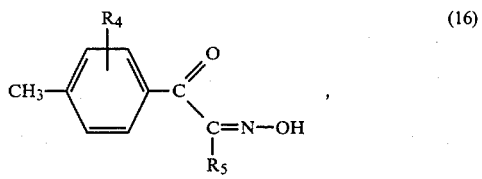 (16)

wherein $R_4$ and $R_5$ are as defined above, with a hydrazine of the formula

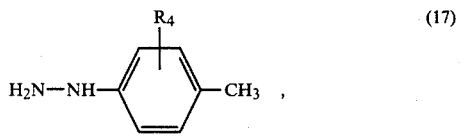 (17)

wherein $R_4$ is as defined above, and cyclising the resultant oxime hydrazone of the formula

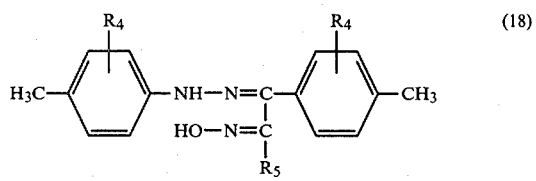 (18)

to give the N-oxidotriazole of the formula

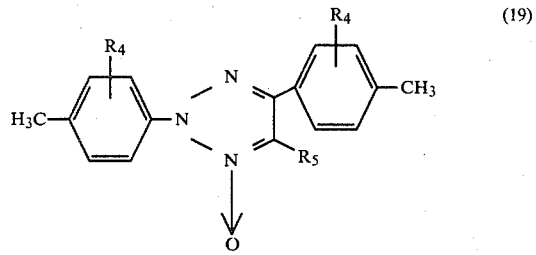 (19)

and reducing this compound to give the corresponding 2,4-bis-(p-tolyl)-2H-1,2,3-triazoles, monohalogenating the methyl groups of these latter and reacting the resultant halogenomethyl compounds either with phosphorus compounds of the formulae

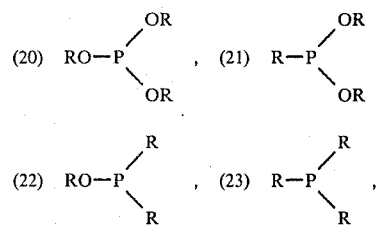

wherein R is as defined above, radicals R bound to oxygen preferably being lower alkyl radicals, radicals R bound to phosphorus on the other hand preferably being aryl radicals, such as phenyl radicals, or reacting them to give the corresponding aldehyde compounds.

Compounds of the formula (14) are obtained by reacting an aromatic amine, such as an optionally substituted amine, with suitable aldehydes.

The novel compounds defined above exhibit a more or less pronounced fluorescent in the dissolved or finely divided state. They can be used for optically brightening a wide variety of synthetic, regenerated man-made or natural organic materials or substances which contain such organic materials.

Without any restriction being implied by the following classification, examples of organic materials which can be optically brightened are:

I. Synthetic organic materials of high molecular weight:

(a) polymerisation products based on organic compounds containing at least one polymerisable carbon-carbon double bond, that is to say their homopolymers or copolymers as well as their aftertreatment products, for example, crosslinking, grafting or degradation products, polymer blends, or products obtained by modification of reactive groups, for example polymers based on $\alpha,\beta$-unsaturated carboxylic acids or derivatives of such carboxylic acids, especially on acrylic compounds, for example acrylic esters, acrylic acid, acrylonitrile, acrylic amides and their derivatives or their methacrylic analogues), on olefin hydrocarbons (for example ethylene, propylene, styrenes or dienes and also ABS polymers), and polymers based on vinyl and vinylidene compounds (for example vinyl chloride, vinyl alcohol and vinylidene chloride);

(b) polymerisation products which can be obtained by ring opening, for example, polyamides of the polycaprolactam type, and also polymers which are obtained both by polyaddition and by polycondensation, for example polyethers or polyacetals;

(c) polycondensation products or precondensates based on bifunctional or polyfunctional compounds with condensable groups, their homocondensation and co-condensation products, and aftertreatment products, for example polyesters, especially saturated polyesters (for example ethylene glycol terephthalic acid polyester) or unsaturated polyesters (for example maleic acid-dialcohol polycondensates as well as their crosslinking products with copolymerisable vinyl monomers), unbranched and branched polyesters (also including those based on polyhydric alcohols, for example alkyd resins), polyamides (for example hexamethylenediamine adipate), maleic resins, melamine resins, their precondensates and analogues, polycarbonates and silicones;

(d) polyaddition products, such as polyurethanes (crosslinked and uncrosslinked) and epoxide resins.

II. Regenerated man-made organic materials, for example, cellulose esters of varying degrees of esterification (so-called 2½-acetate or triacetate) or cellulose ethers, regenerated cellulose (viscose or cuprammonium cellulose), or their aftertreatment products, and casein plastics.

III. Natural organic materials of animal or vegetable origin, for example based on cellulose or proteins, such as cotton, wool, linen, silk, varnish gums, starch and casein.

The organic materials to be optically brightened can be in the most diverse states of processing (raw materials, semi-finished goods or finished goods). On the other hand, they can be in the form of structures of the most diverse shapes, for example predominantly three-dimensional structures such as sheets, profiles, injection mouldings, various machined articles, chips, granules or foams, and also predominently two-dimensional structures, such as films, foils, lacquers, coatings and impregnations or predominantly one-dimensional bodies, such as filaments, fibres, flocks and wires. The said materials can, on the other hand, also be in an unshaped state, in the most diverse homogeneous or inhomogeneous forms of division, as for example in the form of powders, solutions, emulsions, dispersions, latices, pastes or waxes.

Fibrous materials can, for example, be in the form of endless filaments (stretched or unstretched), staple fibres, flocks, hanks, textile filament yarns, threads, non-wovens, felts, waddings, flocked structures or woven textile or bonded textile fabrics, knitted fabrics and papers, cardboards or paper pulps.

The compounds to be used according to the invention are of importance, inter alia, for the treatment of organic textile materials, especially woven textile fabrics. If fibres which can be in the form of staple fibres or endless filaments or in the form of hanks, woven fabrics, knitted fabrics, fleeces, flocked substrates or bonded fabrics, are to be optically brightened according to the invention, this is advantageously effected in an aqueous medium, wherein the compounds in question are present in a finely divided form (suspensions, so-called microdispersions, or optionally solutions). If desired, dispersing agents, stabilisers, wetting agents and further assistants can be added during the treatment.

Depending on the type of brightener compound used, it can be advantageous to carry out the treatment in a neutral or alkaline or acid bath. The treatment is usually carried out at temperatures of 20° to 140° C., for example at the boiling point of the bath or near it (about 90° C.). Solutions or emulsions in organic solvents can also be used for the finishing according to the invention of textile substrates, as is practised in the dyeing industry in so-called solvent dyeing (pad-thermofixation application, or exhaustion dyeing processes in dyeing machines).

The new fluorescent brighteners of the present invention can further be added to, or incorporated in, the materials before or during their shaping. Thus they can for example be added to the compression moulding composition or injection moulding composition during the manufacture of films, sheets (for example incorporated in polyvinyl chloride in a roller mill at elevated temperature) or mouldings.

If the fashioning of man-made synthetic or regenerated man-made organic materials is effected by spinning processes or from spinning solutions/melts, the fluorescent brighteners can be applied by the following processes:

addition to the starting substances (for example monomers) or intermediates (for example precondensates or prepolymers), that is to say before or during the polymerisation, polycondensation or polyaddition, sprinkling in powder form on polymer chips or granules for spinning solutions/melts, bath dyeing of polymer chips or granules for spinning solutions/melts, metered addition to spinning melts or spinning solutions, and application to the spun tow before stretching.

The fluorescent brighteners of the present invention can, for example, also be employed in the following use forms:

(a) in mixtures with dyestuffs (shading) or pigments (coloured pigments or especially, for example, white pigments), or as an additive to dye baths, printing pastes, discharge pastes or reserve pastes, or for the aftertreatment of dyeings, prints or discharge prints;

(b) in mixtures with carriers, wetting agents, plasticisers, swelling agents, antioxidants, ultraviolet absorbers, heat stabilisers and chemical bleaching agents (chlorite bleach or bleaching bath additives);

(c) in admixture with crosslinking agents or finishing agents (for example starch or synthetic finishes), and in combination with a wide variety of textile finishing processes, especially synthetic resin finishes (for example creaseproof finishes such as wash-and-wear, permanent-press or non-iron), as well as flameproof finishes, soft handle finishes, antisoiling finishes or antistatic finishes, or antimicrobial finishes;

(d) incorporation of the fluorescent brighteners into polymeric carriers (polymerisation, polycondensation or polyaddition products, in a dissolved or dispersed form, for use, for example, in coating agents, impregnating agents or binders (solutions, dispersions and emulsions) for textiles, non-wovens, papers and leather;

(e) as additives to master batches;

(f) as additives to a wide variety of industrial products in order to render these more marketable (for example improving the appearance of soaps, detergents, pigments);

(g) in combination with other optically brightening substances;

(h) in spinning bath preparations, that is to say as additives to spinning baths which are used for improving the slip for the further processing of synthetic fibres, or from a special bath before the streching of the fibre;

(i) as scintillators for various purposes of a photographic nature, for example for electrophotographic reproduction or supersensitising;

(j) depending on the substitution as laser dyes.

If the brightening process is combined with textile treatment or finishing methods, the combined treatment can in many cases advantageously be carried out with the aid of appropriate stable preparations which contain the fluorescent brightener compounds in such a concentration that the desired brightening effect is achieved.

In certain cases, the fluorescent brighteners are made fully effective by an aftertreatment. This can be, for example, a chemical treatment (for example acid treatment), a thermal treatment (for example heat) or a combined chemical/thermal treatment. Thus, for example, the appropriate procedure to follow in brightening a number of fibre substrates, for example polyester fibres, with the fluorescent brighteners according to the invention, is to impregnate these fibres with the aqueous dispersions (or optionally also solutions) of the brighteners at temperatures below 75° C., for example at room temperature, and to subject them to a dry heat treatment at temperatures above 100° C., it being generally advisable additionally to dry the fibrous material beforehand at a moderately elevated temperature, for example at not less than 60° C. to about 130° C. The heat treatment in the dry state is then advantageously carried out at temperature between 120° and 225° C., for example by heating in a drying chamber, by ironing within the specified temperature range or by treatment with dry, superheated steam. The drying and dry heat treatment can also be carried out in immediate succession or be combined in a single process stage.

The amount of fluorescent brightener of the present invention to be used, referred to the weight of the material to be brightened, can vary within wide limits. A marked and lasting effect can be obtained even with very insignificant amounts, in certain cases 0.0001 percent by weight. But it is also possible to use amounts of up to app. 0.8 percent by weight and, on occasion, up to app. 2 percent by weight. For most practical purposes, it is preferable to use amounts between 0.005 and 0.5 percent by weight.

For various reasons it is often advantageous not to use the fluorescent brighteners by themselves, i.e. pure, but in admixture with a wide variety of assistants and extenders, for example anhydrous sodium sulphate, sodium sulphate decahydrate, sodium chloride, sodium carbonate, alkali metal phosphates, such as sodium or potassium orthophosphate, sodium or potassium pyrophosphate and sodium or potassium tripolyphosphates or alkali metal silicates.

The fluorescent brighteners of this invention are also particularly suitable for use as additives to wash liquors or heavy duty and domestic detergents, to which they can be added in various ways. They are appropriately added to wash liquors in the form of their solutions in water or organic solvents, or, in a finely divided form, as aqueous dispersions. They are advantageously added to domestic or heavy duty detergents in any stage of the manufacturing process of the detergents, for example to the slurry before the washing powder is atomised, or during the preparation of liquid detergent combinations. They can be added either in the form of a solution or dispersion in water or other solvents or, without assistants, as a dry brightening powder. For example, the brightening agents can be mixed, kneaded or ground with the active detergents and, in this form, admixed with the finishing powder. However, they can also be sprayed in a dissolved or pre-dispersed form on the finished detergent.

Suitable detergents are the known mixtures of active detergents, for example soap in the form of chips and powders, synthetics, soluble salts of sulphonic acid hemiesters of higher fatty alcohols, arylsulphonic acids with higher and/or multiple alkyl substituents, sulphocarboxylic acid esters of medium to higher alcohols, fatty acid acylaminoalkyl- or acylaminoaryl-glycerol sulphonates and phosphoric acid esters of fatty alcohols. Suitable builders which can be used are, for example, alkali metal polyphosphates and polymetaphosphates, alkali metal pyrophosphates, alkali metal salts of carboxymethylcellulose and other soil redeposition inhibitors, and also alkali metal silicates, alkali metal carbonates, alkali metal borates, alkali metal perborates, nitrilotriacetic acid, ethylenediaminetetraacetic acid, and foam stabilisers, such as alkanolamides of higher fatty acids. The detergents can further contain for example: antistatic agents, fat restorative skin protectives, such as lanolin, enzymes, antimicrobial agents, perfumes and colourants.

The new fluorescent brighteners have the particular advantage that they are also active in the presence of active chlorine donors, for example, hypochlorite, and can be used without significant loss of effect in wash liquors containing non-ionic washing agents, for example alkylphenolpolyglycol ethers.

The compounds according to the invention are added in amounts of 0.005 to 1% or more, based on the weight of the liquid or pulverulent finished detergent. Wash liquors which contain the indicated amounts of the claimed fluorescent brighteners impart a brilliant appearance in daylight when used to wash textiles made from cellulose fibres, polyamide fibres, cellulose fibres with a high quality finish, polyester fibres or wool.

The washing treatment is carried out as follows, for example:

The textiles are treated for 1 to 30 minutes at 20° to 100° C. in a wash liquor which contains 1 to 10 g/kg of a built-up composite detergent and 0.05 go 1%, based on the weight of the detergent, of the claimed brightening agents. The liquor ratio can be 1:3 to 1:50. After they have been washed, the textiles are rinsed and dried in the usual manner. The wash liquor can contain 0.2 g/l of active chlorine (for example as hypochlorite) or 0.1 to 2 g/l of sodium perborate as a bleaching additive.

In the following examples, parts and percentages are always by weight, unless otherwise stated. Unless indicated to the contrary, melting points and boiling points are uncorrected.

EXAMPLE 1

To a well stirred solution of 12.8 g of the diphosphonate of the formula

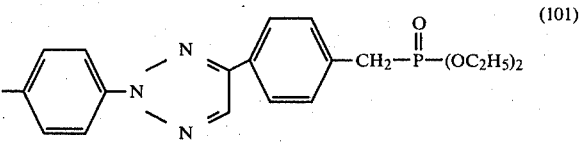

(101)

and 5.8 g of benzaldehyde in 100 ml of dimethyl sulphoxide are added 3.8 g of sodium methylate (content: 92.7%) at 40° to 45° C. in the course of 10 minutes and while expelling the air with nitrogen. The resultant yellow suspension is subsequently stirred for 3 hours at 40° to 45° C. and cooled to approx. 20° C. The crystallised product is collected with suction and dried at 100° to 110° C. in vacuo, affording 3.3 g of the product of the formula

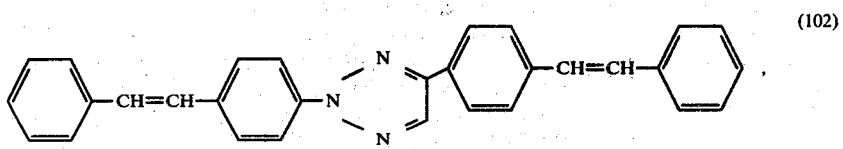

(102)

which is obtained as a light yellow powder with blue fluorescence after recrystallisation from xylene. Melting point: 291°–293° C.

EXAMPLE 2

The procedure of Example 1 is repeated using 25.6 g of the phosphonate of the formula (101), 23.7 g of sodium benzaldehyde-2-sulphonate (content: 96.7%) and 7.6 g of sodium methylate (content: 92.7%) in 100 ml of anhydrous dimethyl formamide. When the reaction is complete, 200 ml of water are slowly added dropwise to the resultant red liquid, which is then neutralised with a small amount of formic acid and cooled. The crystallised product is collected with suction, washed with 500 ml of cold water and dried in vacuo at 100° to 110° C., affording 23.4 g of the compound of the formula

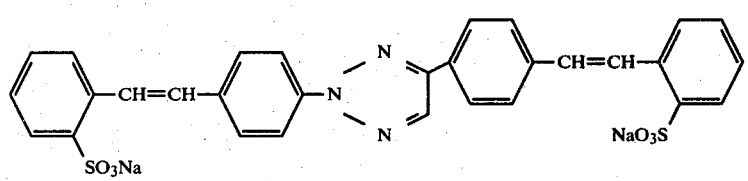

which, after two recrystallisations from a mixture of 7 parts by volume of alcohol and 3 parts by volume of water, is obtained as a pale yellow powder with blue fluorescence. Melting point: >320° C.

The following compounds can be obtained in a manner similar to that described above from the diphosphonate of the formula (101) using the corresponding aldehydes:

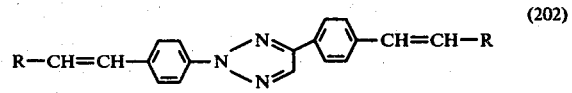

(202)

| No. | R | melting point (°C.) |
|---|---|---|
| 203 | -CN | 293–294 |
| 204 | (benzoxazole) | >350 |
| 205 | -phenyl | >350 |
| 206 | -SO₃Na, NaO₃S- | >300 |
| 207 | -Cl, -Cl, -SO₃Na | >300 |
| 208 | -COOCH₃ | >330 |
| 209 | -SO₂CH₃ | >350 |

(201)

The diphosphonate of the formula (101) can be obtained as follows:

73.5 g of 4-methyl-isonitrosoacetophenone and 65.5 g of p-tolylhydrazine are dissolved in 190 ml of methyl cellosolve with the addition of 3.5 ml of glacial acetic acid and the solution is heated, with stirring, to 80° C. and kept at 80° to 85° C. for 15 minutes. The reaction mixture is then allowed to cool to room temperature with stirring and then further stirred for 15 hours at room temperature. The dark, clear solution is added to a warm mixture of 38° C. of 215 g of crystalline copper sulphate, 270 ml of water and 1000 ml of pyridine. The batch is then heated to 50° C. and kept for 24 hours at 50° to 55° C. After cooling to room temperature, the solution is poured onto a mixture of 2400 ml of conc. hydrochloric acid and 2400 g of ice. The precipitated product is collected with suction, homogenised with 500 ml of filtrate, filtered off by suction once more, washed neutral with water and dried in vacuo at 50° to 60° C., giving 101.8 g of the compound of the formula

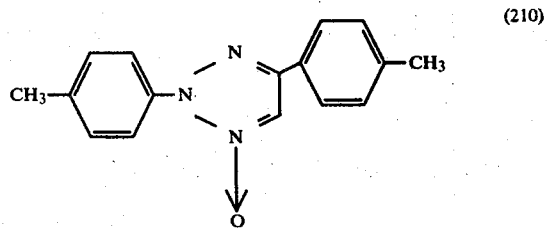

(210)

Melting point: 111°–113° C.

To a warm solution (70° C.) of 101.5 g of the compound of the formula (210) in 500 ml of ethanol are added 50.1 g of zinc dust. Then a mixture of 208 ml of water, 191.2 g of 98% sulphuric acid and 600 ml of ethanol is added dropwise and the batch is stirred for 2 hours at 70° to 77° C. The reaction product is then filtered off hot by suction through a vacuum filter and the residue is washed with 200 ml of boiling ethanol. After cooling, the crystallised product is collected with suction, washed neutral firstly with 200 ml of cold ethanol and then with water and dried in vacuo at 50° to 60° C., giving 69.6 g of 2,4-bis-(p-tolyl)-2H-1,2,3-triazole with a melting point of 98°–99° C.

With stirring, 24.9 g of 2,4-bis-(p-tolyl)-2H-1,2,3-triazole are dissolved in 500 ml of carbon tetrachloride at 71° C. Then 39.2 g of N-bromosuccinimide and 2 g of α,α'-azoisobutyronitrile are added in the course of 10 minutes and the batch is refluxed for 3½ hours. The reaction mixture is filtered hot by suction through a vacuum filter and the residue is washed with 100 ml of hot carbon tetrachloride. The clear filtrate is cooled, the crystallised product filtered off by suction, washed with 2000 ml of warm water and dried in vacuo at 60° to 70° C., affording 21.8 g of 2,4-bis-(4-bromomethyl-phenyl)-2H-1,2,3-triazole with a melting point of 144°–145° C.

117 g of 2,4-bis-(4-bromomethyl-phenyl)-2H-1,2,3-triazole are added at 140° C. in the course of 1 hour to 1000 ml of triethylphosphite. The mixture is then stirred for 6 hours at 140° to 145° C., in the process of which ethyl bromide distills off. After cooling, the solution is concentrated by rotary evaporation and 123.9 g of a colourless liquid are distilled off from the residue under a vacuum of 12 to 13 mm Hg. Yield: 155.9 g of the diphosphonate of the formula (101), which is in the form of a viscous fluid and crystallises completely after a time.

EXAMPLE 3

44.25 g of 4-methyl-isonitrosopropiophenone and 30.5 g of p-tolylhydrazine are stirred for 3 hours at room temperature in 500 ml of glacial acetic acid and then heated for a further 3 hours to 50° C. A pale yellow suspension is obtained. After cooling, the crystalline precipitate which has formed is filtered off by suction, washed with methanol, and dried.

12 g of this 4-methyl-isonitrosopropiophenone-o-tolylhydrazone are dissolved in 20 ml of dimethyl formamide and this solution is added dropwise at 60° C. to a mixture of 30 ml of acetic anhydride and 30 ml of pyridine. The reaction mixture is stirred for 2 hours at 100° C., cooled, and poured onto 1000 ml of ice-water. The crystalline precipitate thereby obtained is recrystallised from methanol to give 2,5-di-(p-tolyl)-4-methyl-v-triazole which melts at 88° to 89° C.

3.3 g of 2,5-di-(p-tolyl)-4-methyl-v-triazole and 5 g of benzaniline are stirred for 1 hour at 60° C. with 6.2 g of potassium tert.-butylate in 50 ml of dimethyl formamide. The reaction mixture turns reddish violet in colour and is poured, with stirring, into 100 ml of 10% hydrochloric acid. The precipitate which forms is collected with suction, washed with water and methanol and recrystallised from chlorobenzene, giving the 2,5-bis-(stilben-4-yl)-4-methyl-v-triazole of the formula

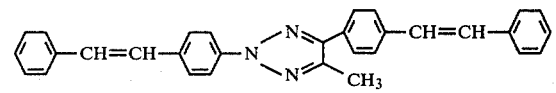

(301)

in the form of light yellow crystals with a melting point of 216°–217° C.

The following compounds can be obtained in a manner similar to that described in this Example:

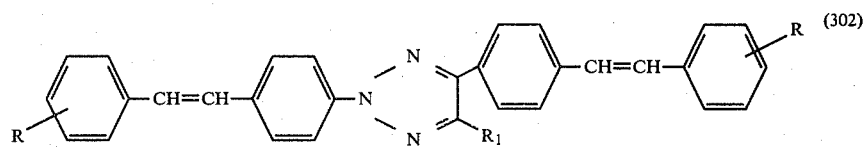

(302)

| No. | R | $R_1$ | melting point (°C.) |
|-----|---|-------|---------------------|
| 303 | p-OCH$_3$ | CH$_3$ | 262–265 |
| 304 | p-Cl | CH$_3$ | 244–246 |
| 305 | p-⌬ | CH$_3$ | >300 |
| 306 | H | ⌬⌬ | 219–220 |
| 307 | p-OCH$_3$ | ⌬⌬ | 223–224 |

EXAMPLE 4

To a well stirred solution of 13.9 g of the phosphonate of the formula

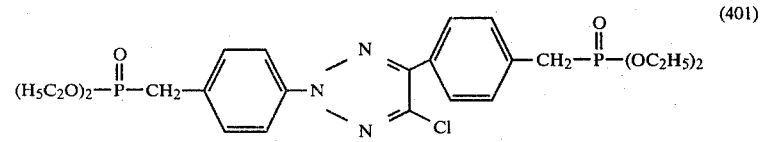

(401)

and 7.2 g of 4-cyanobenzaldehyde in 50 ml of dimethyl formamide are added 3.6 g of sodium methylate (content: 96.7%) at 40° to 45° C. in the course of 15 minutes and while expelling the air with nitrogen. The resultant suspension is stirred for 5 hours at 40° C. to 45° C., poured into 50 ml of methanol, acidified with approx. 1 ml of formic acid, and cooled to approx. 5° C. The crystallised product is filtered by suction, washed with methanol and dried in vacuo at 50° to 60° C., affording 8.9 g of the product of the formula

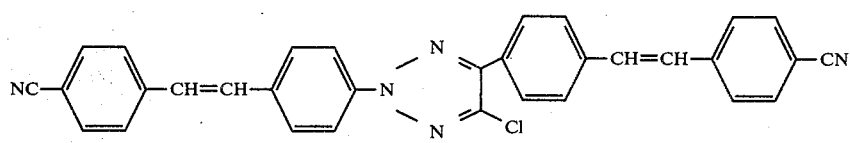
(402)

which, after recrystallisation from o-dichlorobenzene with fuller's earth, is obtained as a yellow crystalline powder with a melting point of 273°–276° C.

The following compounds can be obtained in similar manner from the diphosphonate of the formula (401) using the corresponding aldehydes:

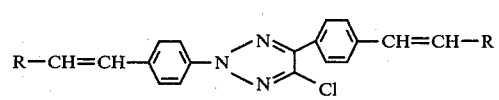
(403)

| No. | R | melting point (°C.) |
|---|---|---|
| (404) | —⟨⟩—COOCH₃ | 273–274 |
| (405) | —⟨⟩—Cl (with Cl) | 247–249 |
| (406) | —⟨⟩—SO₂CH₃ | 309–311 |
| (407) | —⟨⟩—⟨⟩ | >320 |

The diphosphonate of the formula (401) can be obtained as follows:

With stirring, 191 g of the compound of the formula (210) are dissolved at 70° C. in a mixture of 1900 ml of dioxan and 230 ml of water. HCl gas is introduced into this solution at 70° C. to 80° C. over the course of 17 hours. The resultant dark, slightly turbid solution is filtered clear, cooled to approx. 5° C. and then 500 ml of ice-water are added dropwise with stirring. The crystallised product is collected with suction, washed neutral with water, and dried in vacuo at 50° C., giving 181.4 g of the compound of the formula

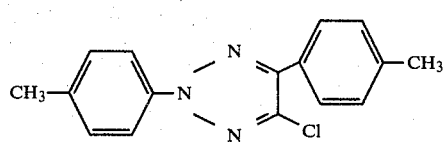
(408)

with a melting point of 110°–112° C.

With stirring, 93.6 g of the compound (408) are dissolved in 700 ml of carbon tetrachloride at 75° C. Then 123 g of N-bromosuccinimide and 6.2 g of α,α'-azoisobutyronitrile are added and the mixture is refluxed for 2 hours. The reaction mixture is filtered hot by suction through a vacuum filter and the filtrate is cooled. The crystallised product is collected with suction, suspended in hot water, filtered off by suction once more, washed well with water and dried in vacuo, giving 84 g of the compound of the formula

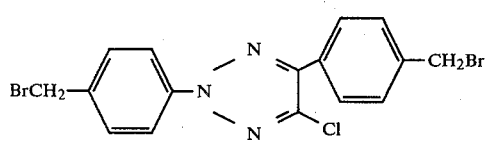
(409)

with a melting point of 144°–145° C.

84 g of the compound of the formula (409) are added at 138° to 144° C. in the course of 1 hour to 700 ml of triethylphosphite. The yellowish, slightly turbid solution is stirred for 6 hours at 148° to 150° C., in the process of which ethyl bromide distills off. After clear filtration, the solution is concentrated by rotary evaporation. A colourless fluid is distilled off from the residue under a vacuum of 15 mm Hg. The residue is treated with 1 liter of petroleum ether and the crystallised product is filtered off by suction, washed well with petroleum ether and dried in vacuo at 50° to 60° C., giving 77.9 g of the compound of the formula (401) with a melting point of 121°–123° C.

EXAMPLE 5

Bleached cotton is washed in the liquor ratio 1:30 for 30 minutes in a warm liquor of 60° C. which contains, per liter, the following ingredients:
  0.032 g of the fluorescent brightener of the formula (201), (206) or (207),
  1 g of active chlorine (Javelle water)
  4 g of a washing powder of the following composition:
    15% of dodecylbenzenesulphonate
    10% of sodium laurylsulphate
    40% of sodium tripolyphosphate
    25.75% of anhydrous sodium sulphate
    7% of sodium metasilicate
    2% of carboxymethyl cellulose
    0.25% of ethylenediaminetetracetic acid.

After it has been rinsed and dried, the fabric has a good white effect of good fastness to acid and chlorine.

The fluorescent brightener of the formula (201), (206) or (207) can also be incorporated direct in the washing powder of the above composition.

A strong white effect is also obtained by carrying out the wash in the same way at 20° C. for 30 minutes.

EXAMPLE 6

A polyamide fabric (Perlon) is put at 60° C., in the liquor ratio of 1:40, into a bath which contains (referred to the weight of the fabric) 0.1% of a fluorescent brightener of the formula (201), (206) or (207) and, per liter, 1 g of 80% acetic acid and 0.25 g of an adduct of 30 to 35 moles of ethylene oxide and 1 mole of commercial stearyl alcohol. The bath is heated within 30 minutes to boiling temperature and kept at the boil for 30 minutes. The fabric is then rinsed and dried. A strong white effect of good light fastness is obtained.

Similar white effects are obtained by using a fabric made of polyamide 66 (nylon) instead of polyamide 6.

Finally, it is also to carry out the process under high temperature conditions, e.g. over the course of 30 minutes at 130° C. For this kind of application it is advisable to add 3 g/l of hydrosulphite to the solution.

EXAMPLE 7

Bleached wool is treated in a liquor ratio of 1:40 for 60 minutes in a bath which contains 0.1% of the fluorescent brightener of the formula (201), based on the weight of the fabric, and 4 g/l of hydrosulphite. After rinsing and drying, strong white effects of good lightfastness are obtained.

Strong white effects are also obtained by adding 5% of acetic acid, based on the weight of the fabric, instead of hydrosulphite to the bath.

EXAMPLE 8

A polyester fabric (e.g. "Dacron") is padded at room temperature with an aqueous dispersion which contains, per liter, 2 g of a compound of the formula (203) as well as 1 g of an adduct of approx. 8 moles of ethylene oxide and 1 mole of p.tert.-octylphenol, and dried at approx. 100° C. The dry material is subsequently subjected to a heat treatment at 150° to 220° C., which lasts from 2 minutes to a few seconds, depending on the temperature. The treated material has a markedly whiter appearance than untreated material.

EXAMPLE 9

A modified polyester fabric (Dacron 64 ®) prepared from co-condensation of 2 to 5 molar percent of isophthalic acid-5-sodium sulphonate is padded to a liquor pick-up of 70% with a liquor containing, per liter, 2.5 g of the compound of the formula (203) and 0.1 g of an adduct of 2 to 5 moles of ethylene oxide and 1 mole of polyphenol. The fabric is dried for 20 minutes at 70° C. The dry fabric is subsequently thermofixed for 30 seconds at 220° C., washed for 30 minutes at 97° C. in a liquor ratio of 1:30 in a wash liquor which contains, per liter, 5 g of soap and 2 g of sodium carbonate, rinsed in running cold water and finally dried with a hot iron at 180° C.

The treated fabric has a markedly whiter appearance than untreated fabric.

EXAMPLE 10

100 Parts of granulated terephthalic acid/ethylene glycol-polyester are homogeneously mixed with 0.05 part of one of the compounds of the formula (203) or (205) in a roller vessel. With stirring, the mixture is fused at 285° C. and spun through spinnerets. Strongly whitened polyester fibres are obtained. The above compound can also be added before or during the polycondensation to the polyester.

EXAMPLE 11

Bleached cotton is put at 20° C. in a liquor ratio of 1:25 into a bath which contains 0.1 to 0.2% of a fluorescent brightener of the formula (201) or (206), based on the weight of the fabric. After heating for 15 minutes to 50° C., 5 g of sodium sulphate per liter of liquor are added. After a further 15 minutes, the fabric is briefly rinsed and dried. THe treated cotton has a good white effect.

EXAMPLE 12

10,000 g of polyamide chips obtained in known manner from hexamethylenediamine adipate are mixed for 12 hours in a roller vessel with 30 g of titanium dioxide (rutile modification) and 5 g of the compound of the formula (203). The treated chips are melted in a boiler which is heated with oil or diphenyl vapour to 300°–310° C., after expulsion of the atmospheric oxygen with steam, and stirred for half an hour. The melt is then pressed out through a spinneret under a nitrogen pressure of 5 atmos. (gauge) and the spun, cooled filament is wound on a spool. The threads obtained exhibit a good white effect.

Similarly good results are obtained by using a polyamide obtained from ε-caprolactam instead of from hexamethylenediamine adipate.

EXAMPLE 13

5 g of the fluorescent brightener of the formula (206) are dissolved in 40 ml of hot distilled water of 90° C. To this solution are then added 1000 ml of an aqueous coating liquor which contains the following constituents:
- 35 g of commercial casein,
- 80 g of a 50% synthetic resin dispersion based on butadiene-styrene polymers (e.g. DOW-LATEX 626 ®, DOW Chemicals, USA),
- 1 g of sodium polyphosphate,
- 2 g of sulphated dodecyl alcohol polyglycol ether with 15 ethylenoxy groups,
- 400 g of aluminum magnesium silicate (China clay), and
- 15 g of conc. ammonia.

The pH value of this dispersion is approx. 9. The surface of sized paper or cardboard is coated with this coating liquor in a size press or other coating machines.

A coated paper of exceptional whiteness is obtained.

EXAMPLE 14

Bleached cotton which has been given a non-iron finish with aminoplast resin is washed in the liquor ratio 1:20 for 15 minutes in a warm liquor of 50° C. which contains, per liter, the following ingredients:
- 0.004 to 0.016 g of the compound of the formula (201), (206) or (207),
- 4 g of a washing powder of the following composition:
  - 15% of dodecylbenzenesulphonate
  - 10% of sodium laurylsulphate
  - 40% of sodium tripolyphosphate
  - 25.75% of anhydrous sodium sulphate
  - 7% of sodium metasilicate
  - 2% of carboxymethyl cellulose
  - 0.25% of ethylenediaminetetracetic acid.

After it has been rinsed and dried, th fabric has a higher white content in daylight than untreated fabric.

EXAMPLE 15

A padding liquor is prepared by dissolving 2 g of the compound of the formula (201) and 2 g of an adduct of approx. 35 moles of ethylene oxide and 1 mole of octadecyl alcohol in 1000 ml of softened water.

A polyamide 6 fabric is padded with this liquor and dried at 160° C. A brilliant white effect is obtained.

EXAMPLE 16

A padding liquor is prepared by dissolving 2 g of the compound of the formula (201), (206) or (207) and 2 g of an adduct of approx. 35 moles of ethylene oxide and 1 mole of octadecyl alcohol in 100 ml of softened water.

A cotton fabric is padded with this liquor and dried at 70° C. A brilliant white effect is obtained.

We claim:

1. 2,4-Bis-(stilben-4'-yl)-v-triazoles of the formula

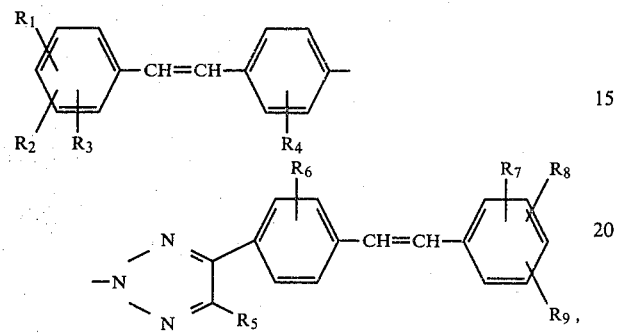

wherein each of $R_1$ and $R_7$ independently represents a hydrogen atom, a sulphonic acid group or its salt selected from the group consisting of alkali metal, alkaline earth metal, ammonium or amine, sulphonamido, a carboxylic acid group or its salt selected from the group consisting of alkali metal, alkaline earth metal, ammonium or amine, carbalkoxy of 2 to 5 carbon atoms or carbonamido, a cyano group, a halogen atom, an unsubstituted or substituted alkylsulphonyl substituted by phenyl, hydroxy, alkanoyloxy of 2 to 15 carbon atoms or halogen, unsubstituted or substituted arylsulphonyl substituted by halogen or alkyl of 1 to 8 carbon atoms, unsubstituted or substituted alkyl substituted by hydroxy, alkoxy of 1 to 4 carbon atoms, cyano, halogen, carboxy, sulfonic acid group, carbalkoxy of 1 to 4 carbon atoms in the alkoxy moiety, phenyl or phenoxy, unsubstituted or substituted alkoxy substituted by hydroxy, alkoxy of 1 to 4 carbon atoms, cyano, halogen, carboxy, carbalkoxy of 1 to 4 carbon atoms in the alkoxy moiety, phenyl or phenoxy, unsubstituted or substituted aralkyl substituted by halogen, cyano, carboxy, carbalkoxy of 1 to 4 carbon atoms in the alkoxy moiety, sulpho, alkyl or alkoxy each of 1 to 4 carbon atoms, unsubstituted or substituted aryl substituted by halogen, cyano, carboxy carbalkoxy of 1 to 4 carbon atoms in the alkoxy moiety, sulpho, alkyl or alkoxy each of 1 to 4 carbon atoms, unsubstituted or substituted aryloxy substituted by halogen, cyano, carboxy, carbalkoxy of 1 to 4 carbon atoms in the alkoxy moiety, sulpho, alkyl or alkoxy each of 1 to 4 carbon atoms, aralkoxy or unsubstituted or substituted cycloalkyl radical substituted by alkyl of 1 to 4 carbon atoms, an unsubstituted or substituted 5-membered heterocyclic ring selected from the group consisting of v-triazole, oxazole or 1,3,4-oxdiazole, said substituted heterocycles are substituted by alkyl of 1 to 4 carbon atoms, halogen, phenyl, carboxy, carbalkoxy of 1 to 4 carbon atoms in the alkoxy moiety, cyano, benzyl, alkoxy of 1 to 4 carbon atoms, phenoxy or sulpho, with two adjacent substituents of the triazole and oxazole together are able to form a fused benzene ring or together with $R_2$ and $R_8$ they represent a methylenedioxy, ethylenedioxy, methylenoxymethylenoxy, trimethylene, tetramethylene, propenylene, butenylene or butadienylene radical, each of $R_2$ and $R_8$ independently represents a hydrogen atom, a sulphonic acid group or its salt selected from the group consisting of alkali metal, alkaline earth metal, ammonium or amine, sulphonamido, a carboxylic acid group or its salt selected from the group consisting of alkali metal, alkaline earth metal, ammonium or amine, carbalkoxy of 2 to 5 carbon atoms or carbonamido, a cyano group, a halogen atom, an unsubstituted or substituted alkyl substituted by hydroxy, alkoxy of 1 to 4 carbon atoms, cyano, halogen, carboxy, sulphonic acid group, carbalkoxy of 1 to 4 carbon atoms in the alkoxy moiety, phenyl or phenoxy, or unsubstituted or substituted alkoxy substituted by hydroxy, alkoxy of 1 to 4 carbon atoms, cyano, halogen, carboxy, carbalkoxy of 1 to 4 carbon atoms in the alkoxy moiety, phenyl or phenoxy, or together with $R_1$ and $R_7$ represent a methylenedioxy, ethylenedioxy, methylenoxymethylenoxy, trimethylene, tetramethylene, propenylene, butenylene or butadienylene radical, each of $R_3$ and $R_9$ independently represents a hydrogen atom, a halogen atom or an unsubstituted or substituted alkyl radical substituted by hydroxy, alkoxy of 1 to 4 carbon atoms, cyano, halogen, carboxy, sulphonic acid group, carbalkoxy of 1 to 4 carbon atoms in the alkoxy moiety phenyl or phenoxy, each of $R_4$ and $R_6$ independently represents a hydrogen atom, a halogen atom, a cyano group, a sulphonic acid group or its salt selected from the group consisting of alkali metal, alkaline earth metal, ammonium or amine, sulphonamido, or a carboxylic acid group or its salt selected from the group consisting of alkali metal, alkaline earth metal, ammonium or amine, carbalkoxy of 2 to 5 carbon atoms or carbonamido, and $R_5$ represents a hydrogen atom, a halogen atom, a cyano group, a sulphonic acid group or its salt selected from the group consisting of alkali metal, alkaline earth metal, ammonium or amine, sulphonamido, a carboxylic acid group or its salt selected from the group consisting of alkali metal, alkaline earth metal, alkaline earth metal, ammonium or amine, carbalkoxy of 2 to 5 carbon atoms or carbonamido, an unsubstituted or substituted alkyl substituted by hydroxy, alkoxy of 1 to 4 carbon atoms, cyano, halogen, carboxy, sulphonic acid group, carbalkoxy of 1 to 4 carbon atoms in the alkoxy moiety, phenyl or phenoxy, unsubstituted or substituted aryl substituted by halogen, cyano, carboxy, carbalkoxy of 1 to 4 carbon atoms in the alkoxy moiety, sulpho, alkyl or alkoxy each of 1 to 4 carbon atoms, unsubstituted or substituted aralkyl substituted by halogen, cyano, carboxy, carbalkoxy of 1 to 4 carbon atoms in the alkoxy moiety, sulpho, alkyl or alkoxy each of 1 to 4 carbon atoms, or unsubstituted or substituted styryl substituted by halogen, cyano, carboxy, carbalkoxy of 1 to 4 carbon atoms in the alkoxy moiety, sulpho, alkyl or alkoxy each of 1 to 4 carbon atoms, or the —CH$_2$OZ group, in which Z represents a hydrogen atom or an unsubstituted or substituted bezoyl or alkanoyl of 2 to 19 carbon atoms.

2. 2,4-Bis-(stilben-4'-yl)-v-triazoles according to claim 1 of the formula

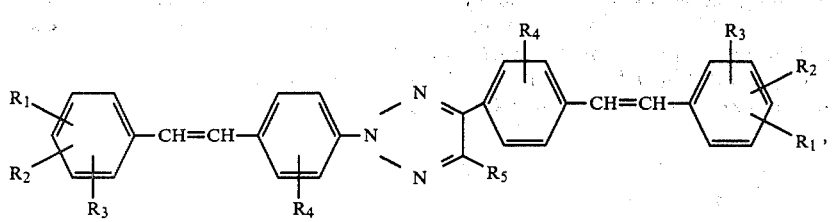

wherein R$_1$, R$_2$, R$_3$, R$_4$ and R$_5$ are as defined in claim 1.

3. 2,4-Bis-(stilben-4'-yl)-v-triazoles according to claim 1 of the formula

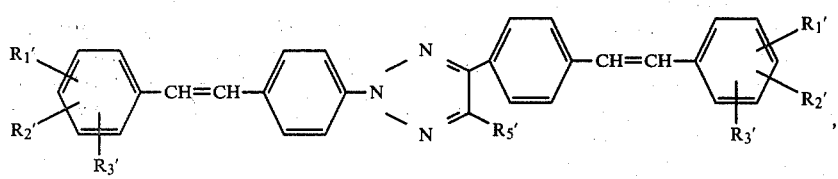

wherein
R$_1$' represents a hydrogen atom, a sulphonic acid group of its salt selected from the group consisting of alkali metal, alkaline earth metal, ammonium or amine, sulphonamido, a carboxylic acid group or its salt selected from the group consisting of alkali metal, alkaline earth metal, ammonium or amine, carbalkoxy of 2 to 5 carbon atoms or carbonamido, a chlorine atom, a cyano group, an alkylsulphonyl group of 1 to 4 carbon atoms, a phenylsulphonyl group, an alkyl or alkoxy of 1 to 4 carbon atoms, a cyclohexyl, benzyl, benzoxazol-2-yl or phenyl, R$_2$' represents a hydrogen atom, a sulphonic acid group or its salt selected from the group consisting of alkali metal, alkaline earth metal, ammonium or amine, a carboxylic acid group or its salt selected from the group consisting of alkali metal, alkaline earth metal, ammonium or amine, carbalkoxy of 2 to 5 carbon atoms or carbonamido, an alkyl of 1 to 4 carbon atoms or a chlorine atom, R$_3$' represents a hydrogen or chlorine atom or an alkyl of 1 to 4 carbon atoms, R$_5$' represents a hydrogen or chlorine atom, a cyano group, a carboxylic acid group or its salt selected from the group consisting of alkali metal, alkaline earth metal, ammonium or amine, carbalkoxy of 2 to 5 carbon atoms or carbonamido, an alkyl of 1 to 6 carbon atoms, a phenyl or benzyl which is unsubstituted or substituted by a chlorine atom or an alkyl of 1 to 4 carbon atoms.

4. 2,4-Bis-(stilben-4'-yl)-v-triazoles according to claim 3 of the formula

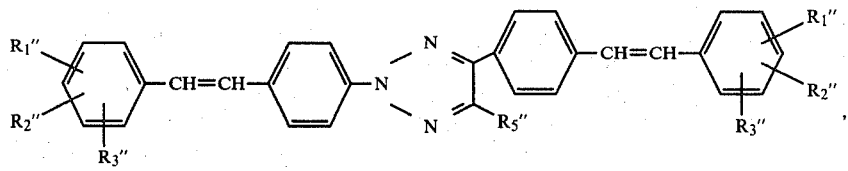

wherein
R$_1$" represents a hydrogen atom, a sulphonic acid group or its salt selected from the group consisting of alkali metal, alkaline earth metal, ammonium or amine, a carbalkoxy group having altogether 2 to 5 carbon atoms, a chlorine atom, a cyano group, an alkylsulphonyl of 1 to 4 carbon atoms, an alkyl or alkoxy each having 1 to 4 carbon atoms, a benzoxazol-2-yl or phenyl, R$_2$" represents a hydrogen atom, a sulphonic acid group or its salt selected from the group consisting of alkali metal, alkaline earth metal, ammonium or amine, or a chlorine atom, R$_3$" represents a hydrogen or chlorine atom, and R$_5$" represents a hydrogen or chlorine atom, an alkyl of 1 to 4 carbon atoms or a phenyl.

5. 2,4-Bis-(stilben-4'-yl)-v-triazoles according to claim 4 of the formula

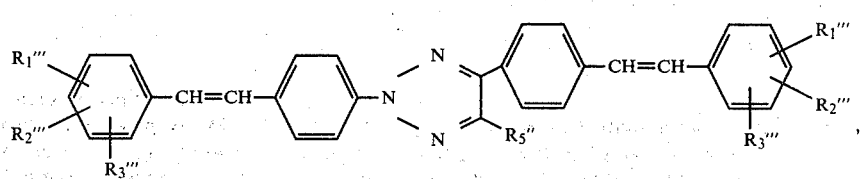

wherein
- $R_1'''$ represents a hydrogen atom, a sulphonic acid group or its salt selected from the group consisting of alkali metal, alkaline earth metal, ammonium or amine, a carbalkoxy group having altogether 2 to 5 carbon atoms, a chlorine atom, a cyano group, an alkylsulphonyl having 1 to 4 cabon atoms, an alkyl or alkoxy each having 1 to 4 carbon atoms, or a phenyl,
- $R_2'''$ represents a sulphonic acid group or its salt selected from the group consisting of alkali metal, alkaline earth metal, ammonium or amine, carbalkoxy group having 2 to 5 carbon atoms or an alkylsulphonyl having 1 to 4 carbon atoms, and
- $R_{12}'$ represents a hydrogen or chlorine atom or a sulphonic acid group or its salt selected from the group consisting of alkali metal, alkaline earth metal, ammonium or amine, whilst at least one of these two symbols represents a sulphonic acid group or its salt selected from the group consisting of alkali metal, alkaline earth metal, ammonium of amine.

8. 2,4-Bis-(stilben-4'-yl)-v-triazoles according to claim 4 of the formula

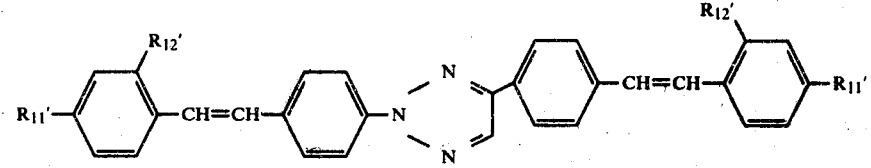

- $R_3'''$ represents a hydrogen or chlorine atom, and
- $R_5'''$ represents a hydrogen or chlorine atom, an alkyl of 1 to 4 carbon atoms, or a phenyl.

6. 2,4-Bis-(stilben-4'-yl)-v-triazoles according to claim 4 of the formula

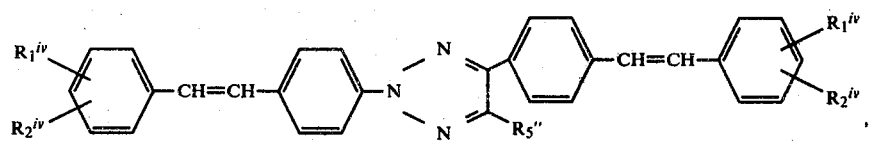

wherein
- $R_1^{iv}$ represents a hydrogen atom, a carbalkoxy group having altogether 2 to 5 carbon atoms, a chlorine atom, a cyano group, an alkylsulphonyl radical having 1 to 4 carbon atoms, an alkyl or alkoxy radical each having 1 to 4 carbon atoms, a benzoxazol-2-yl or phenyl radical,
- $R_2^{iv}$ represents a hydrogen or chlorine atom, and
- $R_5''$ represents a hydrogen or chlorine atom, an alkyl radical of 1 to 4 carbon atoms or a phenyl radical.

7. 2,4-Bis-(stilben-4'-yl)-v-triazoles according to claim 4 of the formula

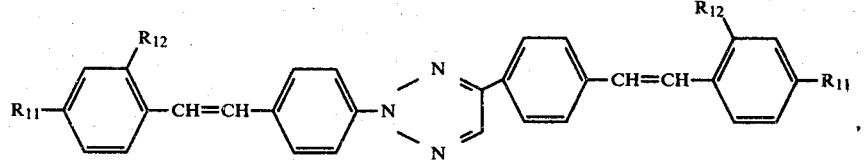

wherein
- $R_{11}'$ represents a hydrogen atom, a sulphonic acid group or its salt selected from the group consisting of alkali metal, alkaline earth metal, ammonium or amine, a cyano group, a phenyl, a chlorine atom, a wherein
- $R_{11}'$ represents a hydrogen atom, a cyano group, a phenyl radical, a chlorine atom, a carbalkoxy radical having 2 to 5 carbon atoms, a benzoxazol-2-yl radical or an alkylsulphonyl radical having 1 to 4 carbon atoms, and
- $R_{12}'$ represents a hydrogen or chlorine atom.

9. 2,4-Bis-(stilben-4'-yl)-v-triazoles according to claim 4 of the formula

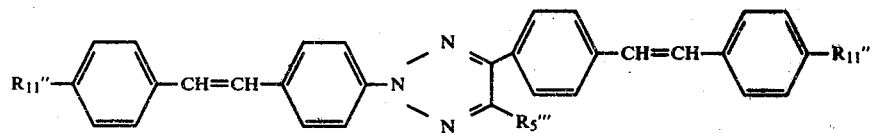

wherein
- $R_{11}''$ represents a cyano group, a carbalkoxy radical of 2 to 5 carbon atoms or an alkylsulphonyl radical of 1 to 4 carbon atoms, and
- $R_5'''$ represents a hydrogen or chlorine atom.

10. A process for optically brightening organic material which comprises incorporating in or applying to said material 2,4-bis-(stilben-4'-yl)-v-triazoles of the formula defined in claim 1.

11. A process according to claim 10 for optically brightening polyester, which comprises incorporating in or applying to the polyester material 2,4-bis-(stilben-4'-yl)-v-triazoles of the formula defined in claim 6.

12. A process according to claim 11, which comprises incorporating the fluorescent brightener in polyester spinning solutions which are then spun.

13. A process according to claim 11, wherein polyester is treated by the pad-heat process.

14. A process according to claim 10, which comprises the use of 0.001 to 2% of the fluorescent brightener, based on the weight of the material to be brightened.

15. A process according to claim 10 for optically brightening cellulose and polyamide materials, which comprises incorporating in or applying to said materials 2,4-bis-(stilben-4'-yl)-v-triazoles of the formula defined in claim 5.

* * * * *

UNITED STATES PATENT AND TRADEMARK OFFICE
CERTIFICATE OF CORRECTION

PATENT NO. : 4,235,741
DATED : NOVEMBER 25, 1980
INVENTOR(S) : KURT WEBER, RUDOLF KIRCHMAYR

It is certified that error appears in the above-identified patent and that said Letters Patent are hereby corrected as shown below:

Claim 5, Column 27, Line 7 reads:

"alkylsulphonyl having 1 to 4 cabon atoms, an alkyl"

Should read:

"alkylsulphonyl having 1 to 4 carbon atoms, an alkyl"

Signed and Sealed this

Third Day of March 1981

[SEAL]

Attest:

RENE D. TEGTMEYER

Attesting Officer    Acting Commissioner of Patents and Trademarks